United States Patent
Timmes et al.

(10) Patent No.: US 7,168,629 B2
(45) Date of Patent: Jan. 30, 2007

(54) SCUBA GEAR SANITIZING METHOD

(76) Inventors: Peter Timmes, 7063 Via Condrejo, Carlsbad, CA (US) 92009; Daniel Timmes, 1129 Bonita Dr., Encinitas, CA (US) 92024

( * ) Notice: Subject to any disclaimer, the term of this patent is extended or adjusted under 35 U.S.C. 154(b) by 0 days.

(21) Appl. No.: 10/199,652

(22) Filed: Jul. 22, 2002

(65) Prior Publication Data
US 2003/0038182 A1    Feb. 27, 2003

Related U.S. Application Data

(63) Continuation-in-part of application No. 09/794,813, filed on Feb. 28, 2001, now abandoned.

(51) Int. Cl.
*A62C 5/02* (2006.01)

(52) U.S. Cl. .............. 239/10; 239/310; 239/318; 239/413; 239/525; 239/602; 239/DIG. 12; 134/22.1; 134/166 R; 134/170

(58) Field of Classification Search .......... 239/1, 239/10, 271, 288, 288.3, 288.5, 310, 318, 239/320, 333, 332, 407, 413, 426, 434, 525, 239/526, 602, DIG. 12, 418, 419.3; 427/2.3; 435/203, 264; 134/22.1, 166 R, 167 R, 170
See application file for complete search history.

(56) References Cited

U.S. PATENT DOCUMENTS 3,215,350 A * 11/1965 Hetrick .................... 239/288.5
3,661,327 A * 5/1972 Adamson et al. ........... 239/571
3,672,380 A * 6/1972 Schuster .................. 239/288.5
4,949,739 A * 8/1990 Ryan ...................... 134/166 R
4,997,000 A * 3/1991 Feast et al. ................ 134/170
5,004,158 A * 4/1991 Halem et al. ............... 239/310
5,011,084 A * 4/1991 Toland ..................... 239/602
5,037,487 A * 8/1991 Santos ..................... 134/22.1
5,045,341 A * 9/1991 Shlenker .................. 427/2.3
5,291,907 A * 3/1994 Clark .................... 134/166 R
5,605,259 A * 2/1997 Clawson et al. ..... 239/DIG. 12
5,975,432 A * 11/1999 Han ....................... 239/526
6,455,017 B1 * 9/2002 Kasting et al. ............ 239/318
6,699,701 B1 * 3/2004 Sulakvelidze et al. ...... 435/263

* cited by examiner

*Primary Examiner*—Steven J. Ganey
(74) *Attorney, Agent, or Firm*—Charmasson, Buchaca & Leach, LLP

(57) ABSTRACT

A method for sanitizing scuba diving equipment including aqua lungs, wet-suits, fins, caps and masks comprises exposing confined parts of the gear such as hoses, pressure regulators and mouthpieces to a pressurized flow of fluid using a fluid-conditioning spray gun adapted to mix a germicidal solution into a jet of water or other fluid carrier. The spray gun has a conical nozzle provided with a set of graduated, flexible, feather-edged disks or barbs that can hermetically mate with a number of scuba diving component apertures of different sizes and shapes.

14 Claims, 2 Drawing Sheets

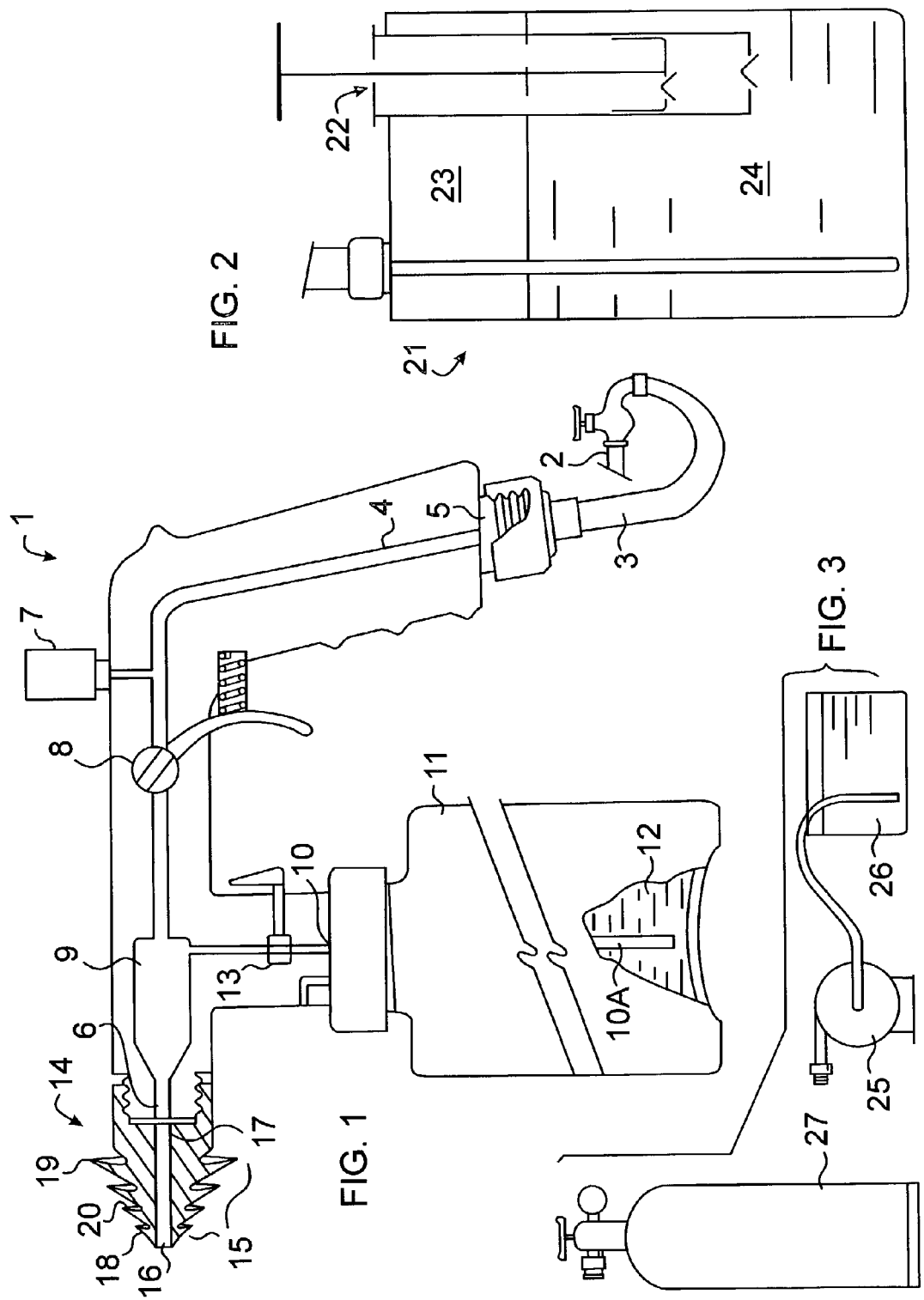

SCUBA GEAR SANITIZING METHOD

PRIOR APPLICATION

This is a continuation-in-part of application Ser. No. 09/794,813 filed Feb. 28, 2001 now abandoned.

FIELD OF THE INVENTION

This invention relates to sanitizing process and devices used in connection with objects that come into intimate contact with the human body such as SCUBA diving gear, and more particularly, to special spraying and atomizing equipment used to apply a sanitizing solution to a contaminated article.

BACKGROUND OF THE INVENTION

The equipment worn by divers such as wet suits, self-contained underwater breathing apparatus best known under the acronym SCUBA or aqualung, the fins and face masks come in intimate contact with various parts of the diver's body. The mouthpiece, tubing, and valve of the aqualung carry fluids and solids exhaled by the diver. The interior of the wet suit comes in contact with bacteria always present about the diver's skin and even infectious discharge from boils, pustules, and fresh wounds. Diving equipment is commonly leased or rented from sporting goods stores and water sport equipment shops found around beaches and aquatic facilities. It is not unusual for a set of scuba gear to be used by several persons over a single day without undergoing any kind of effective sanitization between uses. As reported in the March/April 1997 issue of ALERT DIVER, the contamination risks associated with the use of diving equipment is well recognized. The Center for Disease Control in Atlanta, Georgia has published guidelines for disinfecting scuba equipment. These guidelines include dismantling and scrubbing certain components with soap followed by fresh water rinsing and immersion in a broad spectrum of germicidal solutions. The tedious and time-consuming practices of dismantling and scrubbing parts is seldom followed. The most common method, to date, of sanitization is by immersion into a bath of chlorinated water or similar germicide. It has been found that this type of sanitization is not particularly effective against germs that can invade the complex structure of the aqualung where they can retain their infecting potential for several weeks. Moreover, due to the large amount of sanitizing liquid required in the immersion process, the batch of sanitizing liquid is not replaced after each set of equipment, but, instead, used for long periods of time. Several sets of diving gear may be submerged at the same time, in the same bath. Consequently, the bath may quickly use some of its sanitizing power, and in a worst scenario, contribute to cross-infection from one diver's gear to another. In many cases, diving equipment may be used repetitively by different divers on board ship, or in remote areas where large quantities of sanitizing liquid is not available.

The instant invention results from an attempt to develop a rapid and effective way to sanitize a large variety of diving equipment using a minimum amount of disinfecting fluid.

SUMMARY OF THE INVENTION

The principal and secondary objects of this invention are to provide a method and apparatus for quickly and effectively sanitizing the various pieces of equipment used by scuba divers, or any other equipment worn by a person that comes into intimate contact with human tissue or organ, without requiring dismantling and extensive scrubbing of components, soaking in a large amount of disinfecting fluid, or using complex and bulky equipment, large facilities and intensive labor, in order to minimize or completely prevent cross-infection from one diver to another using the same equipment.

These and other valuable objects are achieved by the use of a fluid-conditioning sprayer operating from a convenient source of pressurized fluid such as urban water supply to effectively inject and disperse a disinfecting solution over broad open surfaces as well as into complex and circuitous passageways. The sprayer nozzle is particularly adapted to intimately engage and seal a plurality of inlets and apertures of the different sizes and shapes and to effectively disperse the spray into a deeply penetrating stream. The nozzle of the sprayer comprises a plurality of gradually decreasing, circumferential and resiliently compressible flanges which can hermetically adhere to various sized openings.

BRIEF DESCRIPTION OF THE DRAWING

FIG. 1 is a cross-sectional view of a sanitizing spray gun according to the invention;

FIG. 2 is a diagrammatical view of a hand-pressurized fluid tank;

FIG. 3 is a diagrammatical view of two alternate sources of pressurized fluid.

DESCRIPTION OF THE EMBODIMENT OF THE INVENTION

Figure 4:
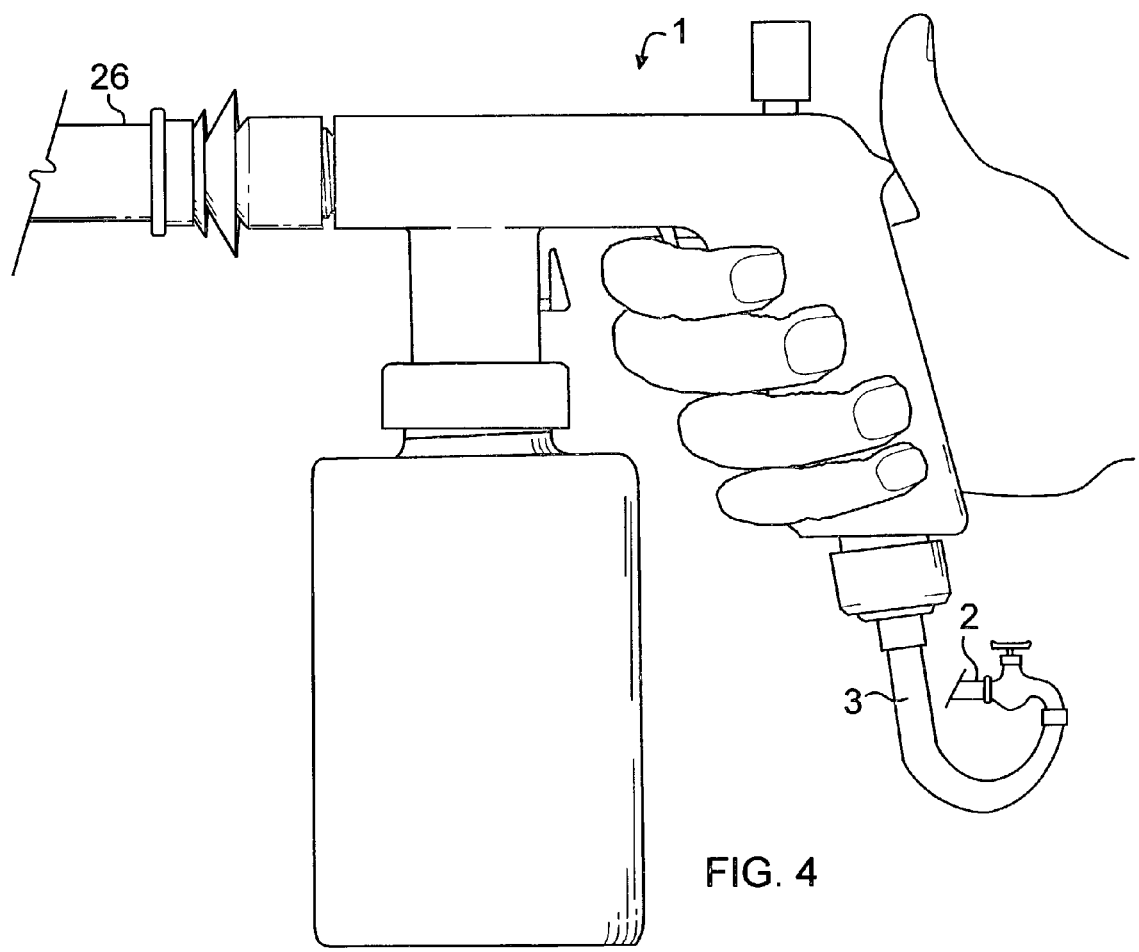
FIG. 4 illustrates the sanitizing of SCUBA gear.

Referring now to the drawing, there is shown an apparatus for sanitizing the various devices and components used in the practice of scuba diving. The apparatus can be effectively used to sanitize wet suits, fins, masks, caps, and more particularly, all the complex components of aqualungs.

The apparatus comprises a spray gun 1 which is connected to a source of pressurized fluid, such as a water line 2 by means of a flexible conduit 3. Inside the spray gun, a pressurized fluid channel 4 runs from a pressurized fluid inlet 5 to a mixed fluid outlet 6, and passes through a variety of control devices. The first of these devices is a manometer 7 which can be monitored to ascertain that the fluid pressure meets the recommended guidelines for each specific sanitizing task. Next is a spring-biased, trigger-controlled valve 8 which can be conveniently activated to admit the pressurized fluid. Finally, a venturi 9 is connected to a mixing fluid inlet 10. Secured to the mixing fluid inlet is a reservoir 11 containing a sanitizing fluid 12. A hand-controlled valve 13 mounted between the venturi 9 and the mixing fluid inlet 10 can be used to either admit, adjust or turn off the supply of sanitizing fluid being drawn from the tank 11 by means of the conduit 10A dripping into the fluid. Screwed upon the mixed fluid outlet 6 is a nozzle 14 specifically configured to provide a relatively leak-proof coupling to apertures of various shapes and sizes. These apertures may belong to hoses, mouthpieces, regulators and other scuba diving components. The nozzle is equipped with a series of size-graduated disks 15 which are axially layered in a sequence of gradually increasing diameters from the distal end 16 of the nozzle toward its proximal end 17. Each disk is circumferentially feather-edged, that is, its thickness decreases radially to a sharpe tip. The disks are made from a resiliently flexible material such as rubber or polypropylene. In the illustrated preferred embodiment, the disks are integrally formed with the nozzle. Typically, the diameter of the channel 4 and nozzle opening is approximately 3 mm. The smallest disk 18 has a diameter of approximately 10 mm, and the largest disk 19 has a diameter of 30 mm. The length 20 of the flexible fins or barbs in the respective disks varies from 3 mm to 10 mm. As the nozzle is introduced into an opening leading to a confined part of a SCUBA gear such such as the end of a hose 26, one or more of the disks is bent backward to form a seal against the internal walls of the opening. In the case when the apparatus is to be used for spraying a wet suit from a short distance, a conventional spraying nozzle such as the ones used in association with garden hoses can be substituted for the above-described self-sealing nozzle 14. Some of those nozzles having a dialable set of various spray patterns, are readily available on the market, such as the Nelson brand of nozzles, model N323S sold by Meijer Lawn & Garden Products (www.meijer.com).

In situations where a source of pressurized fluid is not available, the spray gun 1 may be connected to a pressurable container 21 of the type illustrated in FIG. 2. A hand-operated pump 22 is used to introduce pressurized ambient air into the upper region 23 of the container in order to place the liquid 24 under pressure.

As shown in FIG. 3, the pressurized fluid may be generated by a pump 25 drawing fluid from a tank 26. Alternately, the spray gun 1 may be connected to a bottle 27 of pressurized gas, the gas can be used both as a carrier for the disinfecting solution 12 as well as a drying agent to be blown, without any desanitizing solution, into or over the diving equipment.

The type of santizing solution must be tailored to the type of equipment, taking into account the corrosive property of some particular germicidal agent such as chlorine or providone iodine.

In circumstances when a source of fresh and relatively safe water is not available, the pressurable container 21 of FIG. 2 can be filled with lake or sea water, and the pump 25 of FIG. 3 may draw directly from any available volume of liquid.

The above-described method of sanitizing a piece of equipment that has come into intimate contact with a person's skin or other tissue is more effective than the soaking method so long as the sanitizing solution is applied with enough pressure so as to dislodge and carry debris and other deposits which may have adhered to the equipment. Typically, the solution should be circulated within a regulator, air hose or or other type of passageway under at least 1.36 atmospheres (20 pounds per square inch). The jet of solution sprayed upon a wet suit or any other exposed surface should impact the material with a force of the same order of magnitude. The high pressure circulation or spray needs only last one or two minutes to be effective.

While the preferred embodiment of the invention has been described, modifications can be made and other embodiments may be devised without departing from the spirit of the invention and the scope of the appended claims.

What is claimed is:

1. A method for sanitizing a man-worn article which comprises exposing parts of said article having confined zones to a flow of fluid under pressure, said fluid issuing from a pressurized source, and including an anti-bacterial agent;
    wherein said step of exposing further comprises conditioning said fluid through a spray gun having a fluid outlet and a nozzle at said outlet, said nozzle having a proximal end secured to said outlet and a distal end; and,
    a plurality of circumferentially feather-edged disks axially layered around said nozzle, said disks having different, graduated outer diameters stepping up from a smallest one of said disks proximal to said distal end of a largest one of said disks proximal said proximal end.

2. The method of claim 1, wherein said step of exposing comprises applying at least 1.36 atmospheres to said source.

3. The method of claim 1, wherein said exposing comprises injecting said fluid into a plurality of said confined zones through a leak-proof coupling.

4. The method of claim 3, wherein said step of injecting comprises injecting said fluid into hoses, a pressure regulator and mouthpiece of an aqualung.

5. The method of claim 1, wherein said pressurized source comprises a water supply line.

6. The method of claim 1, wherein said pressurized source comprises a tank of pressurized gas.

7. The method of claim 1, wherein said pressurized source comprises a pump drawing from a body of water.

8. The method of claim 1, wherein said pressurized source comprises:
    a reservoir;
    a liquid held in said reservoir; and
    means for pressurizing said liquid within said reservoir.

9. The method of claim 8, wherein said means for pressurizing comprise a manually operable pump.

10. The method of claim 1, wherein said source comprises:
    a reservoir holding said anti-bacterial agent.

11. A method for sanitizing man-worn articles which comprises exposing parts of each of said articles to a flow of fluid issuing from a pressurized source, said fluid including an anti-bacterial agent;
    wherein said step of exposing comprises applying at least 1.36 atmospheres to said source; and
    injecting said fluid into confined zones of said parts;
    wherein said step of injecting comprises injecting said fluid into hoses, a pressure regulator and a diver's mouthpiece; and
    wherein said step of injecting further comprises conditioning said fluid through a spray gun having a pressurized fluid inlet, a mixed fluid outlet, a pressurized fluid channel including a venturi between said inlet and said outlet, and a mixing fluid inlet connected to said venturi;
    conduit means between said pressurized source and said pressurized fluid inlet, and between a source of said fluid and said mixing fluid inlet; and
    a nozzle at said mixed fluid outlet, said nozzle having a proximal end secured to said outlet and a distal end;
    a plurality of circumferentially feather-edged disks axially layered around said nozzle, said disks having different, graduated outer diameters stepping up from a smallest one of said disks proximal to said distal end of a largest one of said disks proximal said proximal end.

12. The method of claim 11, wherein said disks are made of resiliently flexible material.

13. The method of claim 12, wherein said disks are made of resiliently flexible material.

14. The method of claim 11, wherein said spray gun further comprises a manometer connected to said pressurized fluid channel.

* * * * *